(12) United States Patent
Remmereit et al.

(10) Patent No.: US 8,628,793 B2
(45) Date of Patent: Jan. 14, 2014

(54) NGNA COMPOSITIONS AND METHODS OF USE

(71) Applicant: Life Science Nutrition AS, Hovdebygda (NO)

(72) Inventors: Jan Remmereit, Hovdebygda (NO); Dan Edwall, Djursholm (SE); Anders Struksnes, Oslo (NO)

(73) Assignee: Life Science Nutrition AS, Hovdebygda (NO)

( * ) Notice: Subject to any disclaimer, the term of this patent is extended or adjusted under 35 U.S.C. 154(b) by 0 days.

(21) Appl. No.: 13/720,107

(22) Filed: Dec. 19, 2012

(65) Prior Publication Data
US 2013/0116202 A1     May 9, 2013

Related U.S. Application Data

(63) Continuation of application No. 12/615,818, filed on Nov. 10, 2009.

(60) Provisional application No. 61/113,048, filed on Nov. 10, 2008.

(51) Int. Cl.
*A61K 9/00* (2006.01)
*A61K 31/70* (2006.01)

(52) U.S. Cl.
USPC .............................. 424/434; 424/400; 514/23

(58) Field of Classification Search
None
See application file for complete search history.

(56) References Cited

U.S. PATENT DOCUMENTS

| 7,528,113 | B2 | 5/2009 | Wadell |
| 7,901,715 | B2 | 3/2011 | Remmereit |
| 2005/0148541 | A1* | 7/2005 | Sharma ........................ 514/54 |
| 2005/0159390 | A1 | 7/2005 | Sharma |
| 2005/0201952 | A1 | 9/2005 | Sharma |
| 2009/0238837 | A1* | 9/2009 | Paulson et al. ............. 424/172.1 |

FOREIGN PATENT DOCUMENTS

| WO | 00/38697 | 7/2000 |
| WO | 2006/020210 | 2/2006 |

OTHER PUBLICATIONS

Medeiros, R., et al., "Binding of the hemagglutinin from human or equine influenza H3 viruses to the receptor is altered by substitutions at residue 193", Arch Virol (2004) 149 1663-1671.

* cited by examiner

*Primary Examiner* — Lakshmi Channavajjala
(74) *Attorney, Agent, or Firm* — Casmir Jones SC

(57) ABSTRACT

The present invention relates to the field of viral disorders, and in particular to the use of natural compounds to inhibit viruses and viral infection. Compositions comprising NGNA are provided for treating or preventing viral infections, such as those causing the common cold.

2 Claims, 6 Drawing Sheets

Weight

How was your workout today?

How do you feel?

Do you have a cold 0, or are you healthy 9?

Do you feel the drink helps you?

How is workout energy and joy?

Do you like the sport drink?

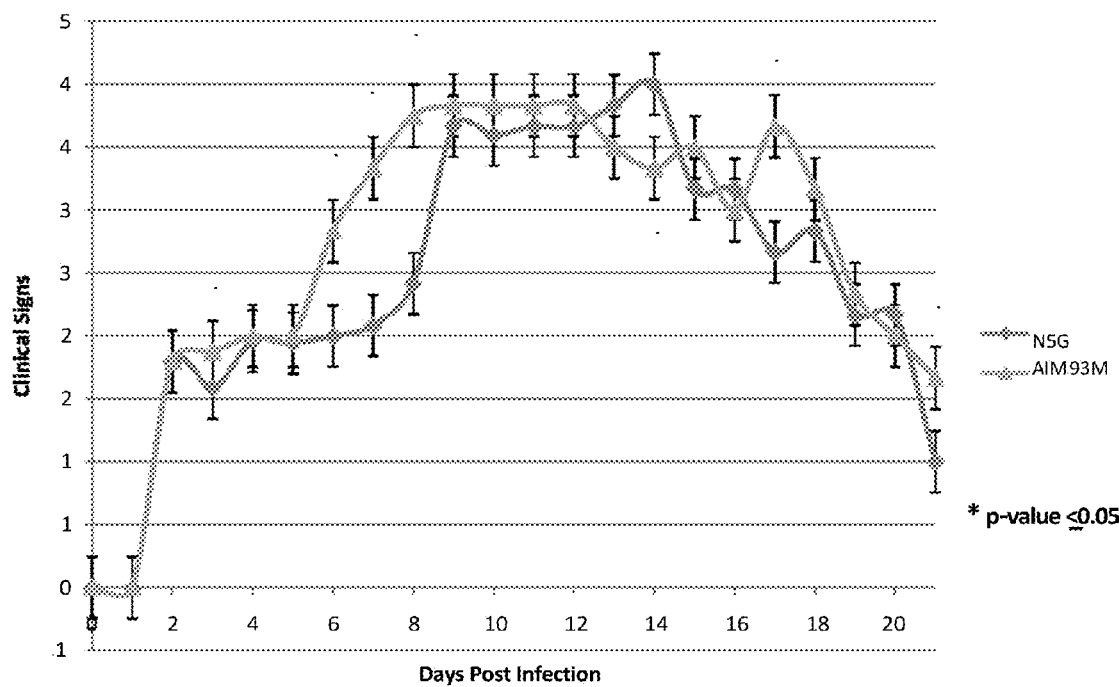
Figure 3  Clinical Signs vs. Days Post Infection
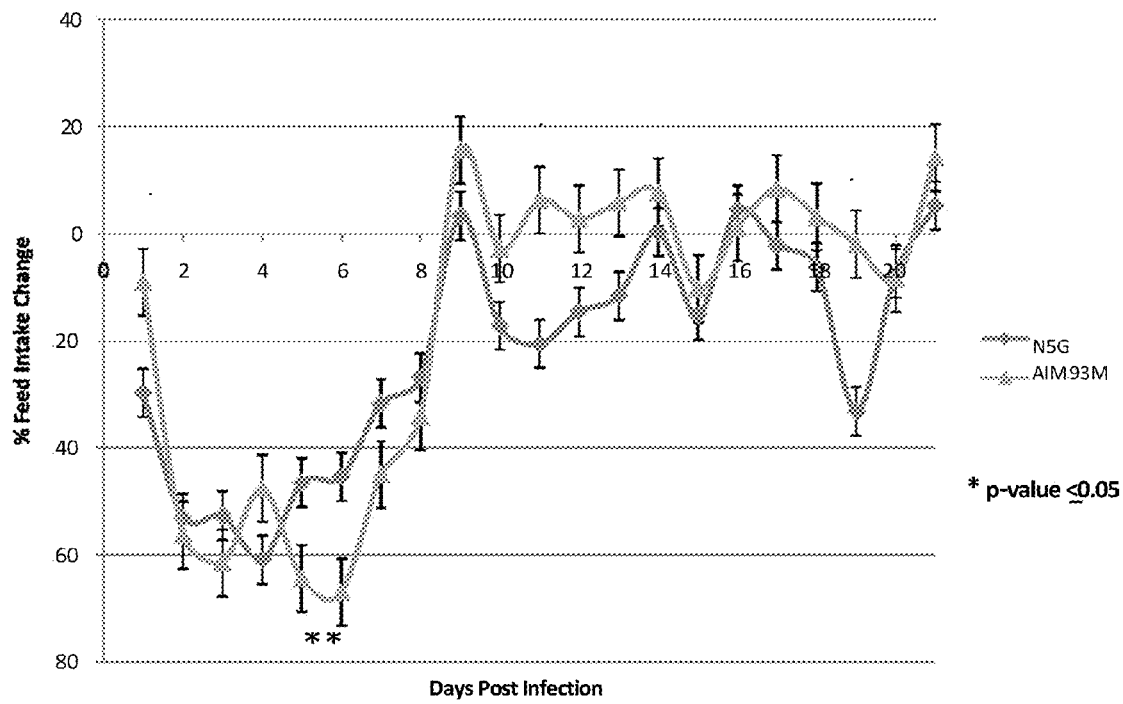
Figure 4  % Feed Intake Change vs. Days Post Infection

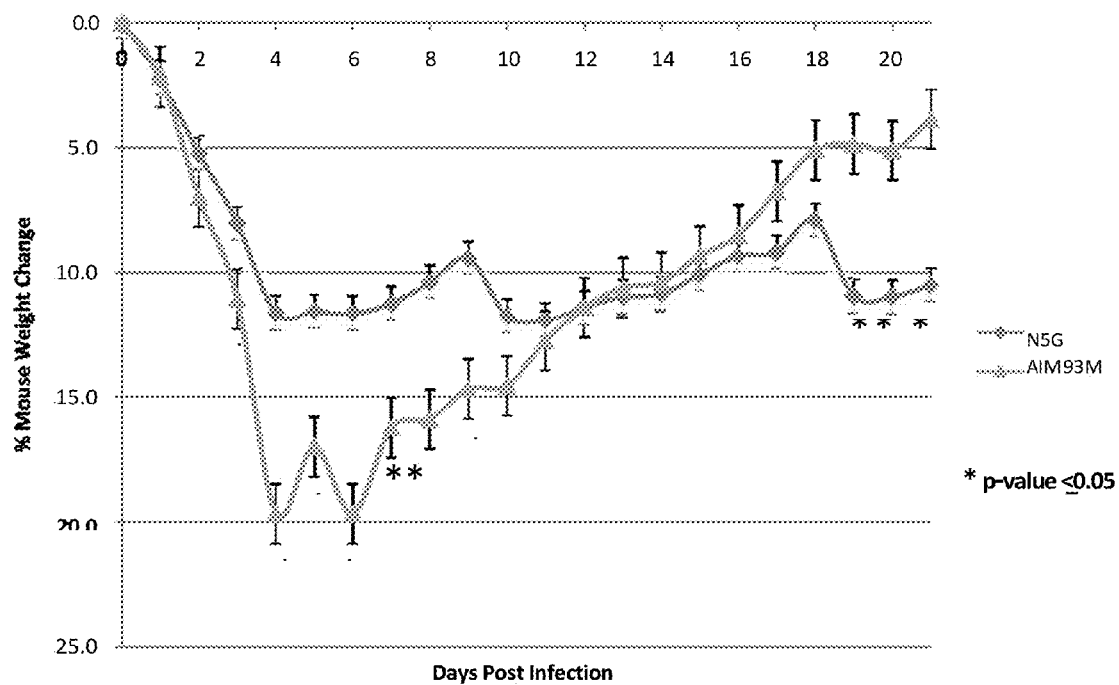
Figure 5 % Mouse Weight Change vs Days Post Infection
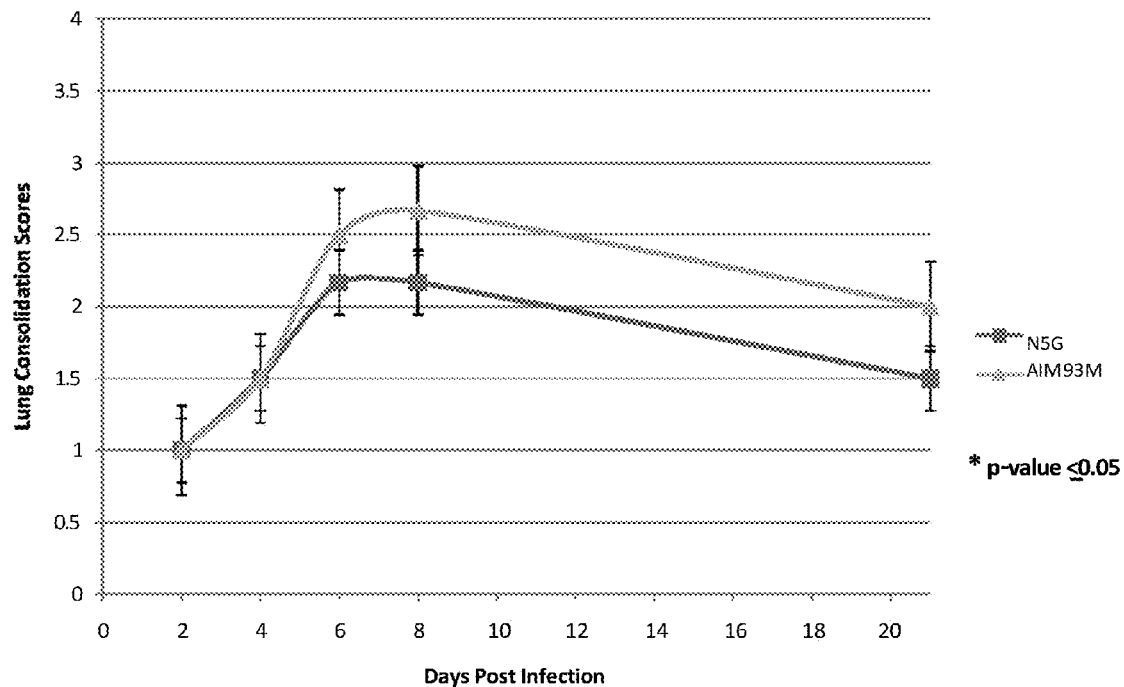
Figure 6 Lung Consolidation Scores vs Days Post Infection

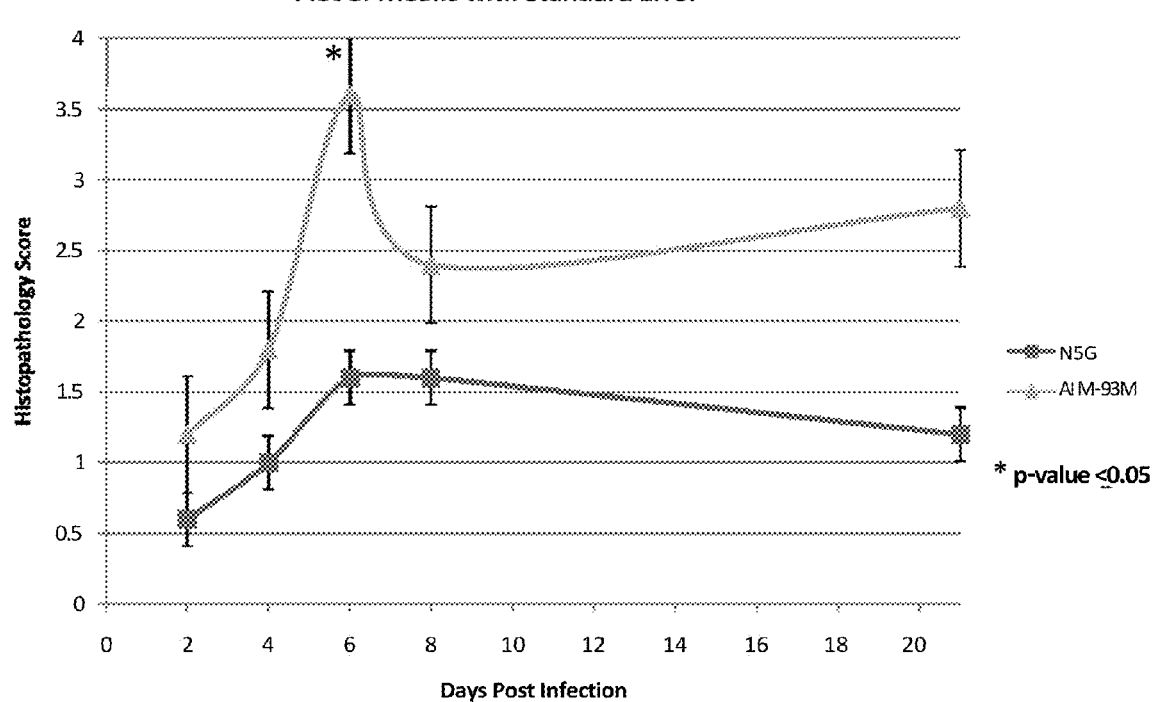

NGNA COMPOSITIONS AND METHODS OF USE

CROSS REFERENCE TO RELATED APPLICATIONS

This application is a continuation of pending U.S. patent application Ser. No. 12/615,818, filed Nov. 10, 2009, which claims priority to expired U.S. Provisional Patent Application Ser. No. 61/113,048, filed Nov. 10, 2008, the contents of which are herein incorporated by reference in their entireties.

FIELD OF THE INVENTION

The present invention relates to the use of compositions comprising n-glycolylneuraminic acid (NGNA). Compositions comprising NGNA find use in inducing physiological responses such as alleviating the symptoms of colds and preventing the onset of colds.

BACKGROUND OF THE INVENTION

In the course of a year, individuals in the United States suffer 1 billion colds, according to some estimates. Colds are most prevalent among children, and seem to be related to youngsters' relative lack of resistance to infection and to contacts with other children in day-care centers and schools. Children have about six to ten colds a year. In families with children in school, the number of colds per child can be as high as 12 a year. Adults average about two to four colds a year, although the range varies widely. Women, especially those aged 20 to 30 years, have more colds than men, possibly because of their closer contact with children. On average, individuals older than 60 have fewer than one cold a year.

The economic impact of the common cold is enormous. The National Center for Health Statistics (NCHS) estimates that, in 1994, 66 million cases of the common cold in the United States required medical attention or resulted in restricted activity. In 1994, colds caused 24 million days of restricted activity and 20 million days lost from school, according to NCHS.

More than 200 different viruses are known to cause the symptoms of the common cold. Some, such as the rhinoviruses, seldom produce serious illnesses. Others, such as parainfluenza and respiratory syncytial virus, produce mild infections in adults but can precipitate severe lower respiratory infections in young children. Rhinoviruses (from the Greek rhin, meaning "nose") cause an estimated 30 to 35 percent of all adult colds, and are most active in early fall, spring and summer More than 110 distinct rhinovirus types have been identified. These agents grow best at temperatures of 33 degrees Celsius [about 91 degrees Fahrenheit (F)], the temperature of the human nasal mucosa. Coronaviruses are believed to cause a large percentage of all adult colds. They induce colds primarily in the winter and early spring. Of the more than 30 isolated strains, three or four infect humans. The importance of coronaviruses as causative agents is hard to assess because, unlike rhinoviruses, they are difficult to grow in the laboratory.

In the United States, most colds occur during the fall and winter. Beginning in late August or early September, the incidence of colds increases slowly for a few weeks and remains high until March or April, when it declines. The seasonal variation may relate to the opening of schools and to cold weather, which prompt people to spend more time indoors and increase the chances that viruses will spread from person to person.

Symptoms of the common cold usually begin two to three days after infection and often include nasal discharge, obstruction of nasal breathing, swelling of the sinus membranes, sneezing, sore throat, cough, and headache. Fever is usually slight but can climb to 102° F. in infants and young children. Cold symptoms can last from two to 14 days, but two-thirds of people recover in a week. If symptoms occur often or last much longer than two weeks, they may be the result of an allergy rather than a cold. Colds occasionally can lead to secondary bacterial infections of the middle ear or sinuses, requiring treatment with antibiotics. High fever, significantly swollen glands, severe facial pain in the sinuses, and a cough that produces mucus, may indicate a complication or more serious illness requiring a doctor's attention.

Viruses cause infection by overcoming the body's complex defense system. The body's first line of defense is mucus, produced by the membranes in the nose and throat. Mucus traps inhaled materials: pollen, dust, bacteria and viruses. When a virus penetrates the mucus and enters a cell, it commandeers the protein-making machinery to manufacture new viruses which, in turn, attack surrounding cells.

Cold symptoms are probably the result of the body's immune response to the viral invasion. Virus-infected cells in the nose send out signals that recruit specialized white blood cells to the site of the infection. In turn, these cells emit a range of immune system chemicals such as kinins. These chemicals probably lead to the symptoms of the common cold by causing swelling and inflammation of the nasal membranes, leakage of proteins and fluid from capillaries and lymph vessels, and the increased production of mucus. Kinins and other chemicals released by immune system cells in the nasal membranes are the subject of intensive research. Researchers are examining whether drugs to block them, or the receptors on cells to which they bind, might benefit people with colds.

Despite the economic and health costs associated with colds, there are very few drugs or natural compounds that have been proven to fight the viruses that cause colds. What is needed in the art are natural compounds for preventing and treating colds.

SUMMARY OF THE INVENTION

The present invention relates to the use of compositions comprising n-glycolylneuraminic acid (NGNA). Compositions comprising NGNA find use in inducing physiological responses such as alleviating the symptoms of viral-induced obesity, alleviating the symptoms of colds, preventing the onset of colds, increasing energy and increasing the feeling of well-being in subjects.

In some embodiments, the present invention provides compositions for treating or preventing colds comprising an effective concentration of n-glycolylneuraminic acid. In some embodiments, the compositions further comprise an excipient. In some embodiments, the compositions are formulated for oral administration. In some embodiments, the compositions are formulated as a tablet. In some embodiments, the compositions are formulated as a capsule. In some embodiments, the compositions further comprise a foodstuff. In some embodiments, the compositions are formulated as a nasal sprays for nasal administration. In some embodiments, the compositions are gels. In some embodiments, the compositions are aqueous solutions. In some embodiments, the compositions are formulated as a pump spray, aerosol spray, gel, powder, lotion, foam or cream for topical or intranasal administration. In some embodiments, the effective concentration is from about 1 nM to about 10 mM.

In some embodiments, the present invention provides methods for treating a human or animal subject comprising providing a composition comprising n-glycolylneuraminic acid in an effective concentration and administering said composition intranasally. In some embodiments, the composition is selected from the group consisting of gels, solutions, sprays, powders, creams, foams and lotions. In some embodiments, the effective concentration is from about 1 nM to about 10 mM.

In some embodiments, the present invention provides compositions for treating or preventing flu comprising an effective concentration of n-glycolylneuraminic acid to destroy or inhibit influenza virus. In some embodiments, the compositions further comprise an excipient. In some embodiments, the compositions are formulated for oral administration. In some embodiments, the compositions are formulated as a tablet. In some embodiments, the compositions are formulated as a capsule. In some embodiments, the compositions further comprise a foodstuff. In some embodiments, the compositions are formulated as a nasal sprays for nasal administration. In some embodiments, the compositions are gels. In some embodiments, the compositions are aqueous solutions. In some embodiments, the compositions are formulated as a pump spray, aerosol spray, gel, powder, lotion, foam or cream for topical or intranasal administration. In some embodiments, the effective concentration is from about 1 nM to about 10 mM. In some embodiments, the influenza virus is selected from the group consisting of Influenza A, B, and C viruses. In some embodiments, the Influenza A virus has a serotype selected from the group consisting of H1N1, H2N2, H3N2, H5N1, H7N7, H1N2, H9N2, H7N2, H7N3, and H10N7 serotypes.

In some embodiments, the present invention provides methods for treating or preventing flu in a human or animal subject comprising providing a composition comprising n-glycolylneuraminic acid in an effective concentration and administering said composition under conditions such that influenza virus is destroyed or inhibited. In some embodiments, the composition is administered intranasally. In some embodiments, the composition is selected from the group consisting of gels, solutions, sprays, powders, creams, foams and lotions. In some embodiments, the effective concentration is from about 1 nM to about 10 mM. In some embodiments, the influenza virus is selected from the group consisting of Influenza A, B, and C viruses. In some embodiments, the Influenza A virus has a serotype selected from the group consisting of H1N1, H2N2, H3N2, H5N1, H7N7, H1N2, H9N2, H7N2, H7N3, and H10N7 serotypes.

In some embodiments, the present invention provides methods of inhibiting a virus comprising contacting said virus with an effective concentration of n-glycolylneuraminic acid, wherein said virus is selected from the group consisting of influenza viruses, rhinoviruses, adenoviruses, herpes viruses and noroviruses. In some embodiments, the effective concentration is from about 1 nM to about 10 mM.

In some embodiments, the present invention provides an animal feed comprising an effective concentration of n-glycolylneuraminic acid.

In some embodiments, the present invention provides a device comprising a solid support having NGNA deposited thereon, wherein said device is configured to cover a body cavity on an animal or human.

In some embodiments, the present invention provides a device for administering an antiviral solution comprising a container containing a solution comprising NGNA and a propellant.

In some embodiments, the present invention provides a device for administering an antiviral solution comprising NGNA comprising a container containing a solution comprising NGNA, a pump and a nozzle, wherein activation of said pump causes said solution comprising NGNA to be expelled through said nozzle.

In some embodiments, the present invention provides a method for treating a site suspected of being contaminated by rhinovirus comprising exposing said site to a composition comprising NGNA under conditions such that the percentage of viable or infectious rhinovirus is decreased. In some embodiments, the site is a surface. In some embodiments, the site is an enclosed space. In some embodiments, the enclosed space is a room. In some embodiments, the enclosed space is a vehicle. In some embodiments, the composition comprising NGNA is provided as an aerosol spray. In some embodiments, the composition comprising NGNA is provided as a foam.

In some embodiments, the present invention provides an NGNA composition for use in treating or preventing infection by influenza virus. In some embodiments, the NGNA composition is provided as an eyedrop, gel, solution, pump spray, aerosol spray, powder, cream, foam or lotion. In some embodiments, the present invention contemplates use of NGNA for the manufacture of a medicament for treating or preventing infection by influenza virus.

DESCRIPTION OF THE FIGURES

FIG. 2a—How was your workout today?; FIG. 2b—How do you feel?; FIG. 2c: Do you have a cold 0, or are you healthy 9?; FIG. 2d: Do you feel the drink helps you? FIG. 2e—How is workout energy and joy?; and FIG. 2F—Do you like the sport drink?. The test subject were asked to rate their responses to these questions on a scale of 0-9, 9 being the most positive.

FIG. 3 is graph of Clinical Signs vs. Days Post Infection.

FIG. 4 is a graph of % Feed Intake Change vs. Days Post Infection.

FIG. 5 is a graph of % Mouse Weight Change vs Days Post Infection.

FIG. 6 is a graph of Lung Consolidation Scores vs Days Post Infection.

FIG. 7 is a graph of Histopathology vs Days Post Infection.

DEFINITIONS

Figure 1A:
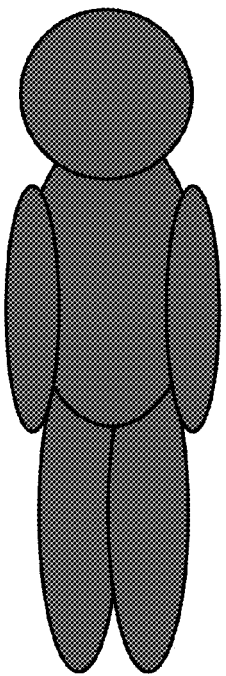
FIG. 1a provides a chart showing body composition before (Før) and after (etter) the eight week NGNA sport drink study.

As used herein, the term "obesity" and related terms refers to an increase in body weight beyond the limitation of skeletal and physical requirement, as the result of an excessive accumulation of fat in the body.

As used herein, the term "anorectic agent" and related terms refer to pharmaceutical agents used to induce weight loss in a subject. Examples of anorectic agents include, but are not limited to, phentermine, phenylpropanolaminea, mazindol, ephedra, and sibutramine.

As used herein, the term "phytonutrient" refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

As used herein, the term "functional foods" refers to food products that include biologically active nutraceutical agents.

As used herein, the terms "nutraceutical agent," and related terms, refer to natural, bioactive chemical compounds that have health promoting, disease preventing or medicinal properties. Examples of nutraceutical agents include, but are not limited to, *Allium Cepa, Allium Sativum, Aloe Vera, Angelica* Species, Naturally Occurring Antioxidants, *Aspergillus Oryzae Enzyme Therapy*, barley grass, Bromelain, Carnitine, Carotenoids and *Flavonoids*, *Catechin*, *Centella Asiatica* (Gotu kola), *Coenzyme Q10*, *Chinese Prepared Medicines*, *Coleus Forskohlii, Commiphora Mukul, Crataegus Oxyacantha* (Hawthorne), *Curcuma Longa* (Turmeric), *Echinacea* Species (Purple Coneflower), *Eleutherococcus Senticosus* (Siberian Ginseng), *Ephedra Species*, Dietary Fish Oil Consumption and Fish Oil Supplementation, *Genistein, Ginkgo Biloba, Glycyrrhiza* (Licorice), *Hypericum Perforatum* (St. John's Wort), *Hydrastis* (Goldenseal) and Other Berberine-Containing Plants, *Lactobacillus, Lobelia* (Indian Tobacco), *Melaleuca Alternifolia, Mentha Piperita*, NGNA, *Panax Ginseng, Pancreatic Enzymes, Piper Mythisticum, Procyanidolic Oligomers, Pygeum Africanum, Quercetin, Sarsaparilla Species, Serenoa Repens* (Saw palmetto, Sabal serrulata), *Silybum Marianum* (Milk Thistle), *Rosemary/Lemon balm, Selenite, Tabebuia Avellanedae* (LaPacho), *Taraxacum Officinale, Tanacetum Parthenium* (Feverfew), *Taxol, Uva Ursi* (Bearberry), *Vaccinium Myrtillus* (Blueberry), *Valerian Officinalis, Viscum Album* (Mistletoe), Vitamin A, Beta-Carotene and Other Carotenoids, and *Zingiber Officinale* (Ginger).

As used herein, the term "weight loss diet regimen" or related terms, is used broadly to include any type of weight loss plan used by a subject. Examples of weight loss diet regimens include, but are not limited to, Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, Zone diet, running, swimming, meditation, yoga, hypnosis, clinical therapy, bicycling, walking, hypnosis, rehabilitation training, a dietary plan provided through a dietician, and surgical procedures.

As used herein, the terms "subject" and "patient" refer to any animal, such as a mammal like a dog, cat, bird, livestock, and preferably a human. Specific examples of "subjects" and "patients" include, but are not limited to, individuals suffering from viral obesity.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

The present invention relates to the field of nutraceuticals, and in particular to nutraceuticals comprising n-glycolylneuraminic acid (NGNA). Compositions comprising NGNA find use in inducing physiological responses such as alleviating the symptoms of viral-induced obesity, alleviating the symptoms of colds, preventing the onset of colds, increasing energy and increasing the feeling of well-being in subjects.

A. Treatment and Prevention of Viral Infection

Despite many decades of research there are still relatively few effective anti-viral compounds in comparison to the human disease burden inflicted by viruses. Coupled with the high mutation rate of certain viruses, which enable anti-viral resistant mutants to arise with alarming speed and frequency, the need for a generic anti-viral agent is as important now as it ever has been.

Influenza has been established as a serious human affliction that can cause localized epidemics and global pandemics of acute respiratory infections. Each year the Influenza virus is responsible for 20,000 to 40,000 deaths and up to 300,000 hospitalization cases in the United States (Sandhu & Mossad, 2001). In the pandemic of 1918 it is widely believed that in excess of 40 million people died. Although children and younger adults experience more cases of infection, severe illness is more common in the elderly, immunocompromised individuals, or those with chronic illnesses such as asthma, diabetes, kidney failure and heart disease. The annual epidemics run from November to March in the Northern Hemisphere, and from April to September in the Southern Hemisphere (Cox N.J & Subbarao K, 2000).

The two classes of Influenza viruses that are responsible for significant human disease are termed Influenza A and Influenza B viruses. Influenza B viruses are thought to only infect humans whereas Influenza A viruses are known to infect a wide variety of animal species. Both are responsible for seasonal epidemics and, as such, are included in the annual influenza vaccines.

Herpes Simplex Virus type 1 (HSV-1) is a member of Herpesviridae, which causes infections in humans. HSV-1 has a worldwide distribution with an estimated 60-95% of the adult population infected (Brady, R. C. & Bernstein, D. I., 2004). HSV-1 is frequently associated with oral disease, normally resulting in the formation of facial lesions. This is an important neurotropic virus which can infect the central nervous system (Immergluck et al.,1998). Once access is gained by the virus to the neurons in sensory ganglia a latent infection can be established (Kramer et al., 2003). Very little is known about the biological processes involved, but under certain stress conditions reactivation is triggered, typically resulting in the reemergence of the external lesions (Itzhaki & Lin, 1998; Qiu and Abdel-Meguid 1999).

Human Rhinoviruses (HRV) are a member of the Picornaviridae. There have been more than 100 different serotypes identified to date. This diverse family of viruses is thought to be responsible for more than 80% of upper respiratory tract infections (Heikkinen & Jarvinen, 2003). As the predominant cause of the common cold, Rhinoviruses are a major human pathogen both in terms of the disease they cause and the economic impact on society.

Adenoviruses are a group of viruses which cause a wide range of diseases. They are known to infect the lining of the eyes, the respiratory tract, the intestines, and the urinary tract and are also one of the causative agents of common cold symptoms. The virus can be split into six sub-groups from A to F based on biological and antigenic characteristics (Horwitz, 1996; Shenk 1996). Treatment advice for adenovirus infection is usually bed rest and associated with the treatment of the symptoms, as at present there is no effective specific antiviral for this virus.

Noroviruses are the most common cause of viral gastroenteritis (Caul et al., 1993; Hedberg & Osterholm, 1993). Consequently, Norovirus is sometimes known as the 'winter vomiting virus' because it is more evident during the winter period. The virus is extremely contagious and is found in the vomit and faeces of infected individuals. Currently, Noroviruses cannot be grown in the laboratory by conventional means. However, in the last year some progress has been made on propagation techniques that involve the use of bioreactors with small intestinal epithelial cells (Straub et al., 2007). However, currently, it is necessary to use a surrogate virus to test the potential virucidal effects against Noroviruses. The most established of the surrogate Norovirus viruses is the Feline Calicivirus, which like Norovirus, belongs to the Caliciviridae family of viruses (Slomka et al., 1998; Doultree et al., 1999).

In some preferred embodiments, the present invention provides NGNA compositions methods of using NGNA compositions for the prevention and/or treatment of viral infections caused by members of the following families of viruses: Picornaviridae, Caliciviridae, Adenoviridae, Herpesviridae, and Orthomyxoviridae. NGNA is a compound that is found naturally in sea cucumbers. NGNA is also found on the surface of all mammalian cells except for humans and chimpanzees and it is thought to act as a viral decoy or scavenger receptor. In some preferred embodiments, the present invention provides NGNA compositions methods of using NGNA compositions for the prevention and/or treatment of viral infections caused by the following viruses: Influenza A, B and C viruses and Asian bird flu viruses (e.g., viruses from the family Orthomyxoviridae, and in particular Influenza A serotypes H1N1, H2N2, H3N2, H5N1, H7N7, H1N2, H9N2, H7N2, H7N3, and H10N7), Herpes Simplex Virus-1 (HSV-1), Rhinoviruses (such as Human Rhinovirus, HRV), Adenoviruses, and Noroviruses. Exemplary formulations are described in detail below. However, in some embodiments, NGNA is formulated as a lotion, spray, gel, ointment, powder, aqueous or non-aqueous solution for topical, intranasal, intravaginal, intraanal, or sublingual administration; as a capsule, powder, or tablet for enteral administration; or as a solution for parenteral administration.

B. Viral Obesity

In the U.S., the prevalence of obesity increased by 30% from 1980 to 1990, and this increase appears to be continuing. One etiology of human obesity is of infectious origin (see, e.g., Dhurandhar, N. (2001) J. Nutr. 131: 2794S-2797S; herein incorporated by reference in its entirety). Six pathogens are reported to cause obesity in animals. Canine distemper virus was the first virus reported to cause obesity in mice (see e.g., Lyons M., et al., (1982) Science 216:82-85; Bernard A., et al., (1988) Comp. Biochem. Physiol. 91B:691-696; Bernard A., et al., (1991) Virology 313:545-551; Bernard A., et al., (1993) J. Neuropath. Exp. Neuro. 52:471-480; McFerran J., et al., (1975) Am. J. Vet. Res. 36:527-534; Bernard A., et al., (1999) J. Virology 73(9):7317-7327; each herein incorporated by reference in their entireties), followed by the avian retrovirus Rous-associated virus-7 shown to cause stunting, obesity and hyperlipidemia in chickens (see e.g., Carter J. K., et al., (1983) Infect. Immun. 39:410-422; Carter J. K., et al., (1983) Avian Dis 27:317-322; each herein incorporated by reference in their entireties). The obesity-promoting effect of Borna disease virus has been demonstrated in rats (see e.g., Gosztonyi G. & Ludwig H. (1995) Current Topics in Microbiol. Immunol. 190:39-73; Fabricant C. G., et al., (1983) Federation Proc 42:2476-2479; each herein incorporated by reference in their entireties). Scrapie agents were reported to induce obesity in mice and hamsters (see e.g., Kim Y. S., et al., (1987) J. Infect. Dis. Aug; 156(2):402-405; Carp R. L., et al., (1990) J. Infect. Dis. 161(3):462-466; Carp R. L., et al., (1998) J. Gen. Virol. 79(Pt 11):2863-2869; Kim Y. S., et al., Proc. Soc. Exp. Biol. Med. 189(1):21-27; each herein incorporated by reference in their entireties). The final two reports were of SMAM-1, an avian adenovirus (see e.g., Dhurandhar N. V., et al., (1990) J. Bombay Vet. College 2:131-132; Dhurandhar N. V., et al., (1992) Vet. Microbiol. 31:101-107; Ajinkya S. M. (1985) Final Technical Report, ICAR 1985: 13-43 Red and Blue Cross Publishing Bombay, India; each herein incorporated by reference in their entireties), and Ad-36 (see e.g., Dhurandhar N. V., et al., (2000) Int. J. Obesity 24:989-996; Dhurandhar N. V., et al., (2001) Int. J. Obesity 25:990-996; Kolesar J. M., et al., (2000) J. Chromatog. B. 744:1-8; herein incorporated by reference in its entirety), a human adenovirus that caused obesity in animals. Additionally, an association with human obesity is the unique feature of SMAM-1 (see, e.g., Dhurandhar N. V., et al., (1997) Obesity Res 5:464-469; herein incorporated by reference in its entirety) and Ad-36 (see, e.g., Vangipuram, S. D., et al., (2004) Obesity Research 12:770-777; Dhurandhar, N. V., et al., (2002) J. Nutr. 132:3155-3160; Atkinson R. L., et al., (1998) Int. J. Obesity 22:S57; Dhurandhar N. V., et al. (1997) FASEB J 3:A230; Atkinson R. L., et al., (2000) Int. J. Obesity suppl 1:S39; Dhurandhar N. V., et al.; (1999) FASEB J 13(4): A369; each herein incorporated by reference in their entireties).

U.S. Pat. Nos. 6,127,113 and 6,664,050, each herein incorporated by reference in their entireties, characterize Ad-36 induced viral obesity. In particular, humans who suffer from viral obesity (i.e., obesity caused by a virus) have, on the average, significantly lower triglycerides (TG), cholesterol (CHOL) and low-density-lipoprotein-associated cholesterol (LDL-CHOL) levels than persons who suffer from obesity that is not viral. In fact, the average TG, CHOL and LDL-CHOL levels of persons with viral obesity are within the normal ranges for persons who are not obese. Diagnostic and screening approaches for Ad-36 and Ad-36p are provided. Anti-obesity vaccines, wherein inactivated viral nucleic acid (e.g., Ad-36 nucleic acid) is administered to a subject, are also described.

C. Formulation of NGNA Compositions

NGNA compositions of the present invention may be delivered in any suitable format. In some embodiments, NGNA is provided from sea cucumbers, e.g., an extract of sea cucumbers, or is prepared from chitin. In some embodiments, the NGNA is preferably about greater than 90%, 95%, 99% or 99.9% pure. In some embodiments, the NGNA is HPLC purified. In some embodiments, NGNA is prepared as described in WO 00/38967, incorporated by reference herein its entirety. For example, N-glycolylneuraminic acid can be purchased commercially from, for example, Sigma Chemical Company, St. Louis, Mo. N-glycolylneuraminic acid also can be synthesized. For example, CMP-N-acetylneuraminic acid hydroxylase can be used to synthesize N-glycolylneurarninic acid as its CMP-glycoside. See, Schlenzka et al., Glycobiolog, 1994, 4(5):675-683. Non-enzymatic methods of synthesis include, for example, synthesis from N-acetylneuraminic acid using methanol or hydrochloric acid and benzylalcohol. Other synthesis methods are described in Choi et al., J. Org. Chem., 1996, 61:8/39 (from mannosamine), Faillard et al., J. Physiol. Chem.' 1965, 344:167 (from glucosamine), U.S. Pat. No. 4,774,326 and U.S. Pat. No.4,774,327, both of which are incorporated by reference herein in their entirety.

In some embodiments, the NGNA compositions are provided in an aqueous solution, including gels, suitable for use as a spray or mist. In some embodiments, the aqueous NGNA solution is incorporated into a pump-spray container, such as precompression pump, or a device such as a nebulizer or cold mist system, for delivery into the nose, mouth or lungs as a fine mist or spray.

In some embodiments, the NGNA compositions of the present invention contain a pharmaceutically acceptable excipient which is effective in forming a thixotropic suspension of the solid particles of medicament comprising the composition, such as those described in U.S. Pat. No. 7,122,206. The excipient is preferably present in an amount which maintains the particles of medicament suspended in the composition during non-use and during spray of the composition into the nasal cavity, and also when the composition is deposited on the mucosal surfaces of the nasal cavities. In some embodiments, the viscosity of the composition at rest is relatively high, for example, about 400 to about 1000 cp. As the composition is subjected to shear forces, for example, upon being subjected to forces involved in its being agitated before spraying, the viscosity of the composition decreases (for example, to about 50 to about 200 cp) and it flows readily through the spray device and exits therefrom in the form of a fine plume which infiltrates and deposits on the mucosal surfaces of at least the following parts of the nose: the anterior regions of the nose (frontal nasal cavities); the frontal sinus; the maxillary sinuses; and the turbinates which overlie the conchas of the nasal cavities. Thus, the NGNA compositions comprise a freely flowable liquid, and in sprayed form, a fine mist that finds its way to and deposits on the desired mucosa. In deposited and relatively unstressed form, the composition increases in viscosity and assumes its gel-like form which includes particles of the medicament suspended therein and which resists being cleared from the nasal passages by the inherent mucocillary forces that are present in the nasal cavities.

Any pharmaceutically acceptable material which is capable of maintaining the solid particles of medicament dispersed substantially uniformly in the composition and of imparting to the composition desired thixotropic properties can be used. Such material is referred to as a "suspending agent". Examples of suspending agents include carboxmethylcellulose, veegum, tragacanth, bentonite, methylcellulose, and polyethylene glycols. A preferred suspending agent is a mixture of microcrystalline cellulose and carboxymethylcellulose, the former being present preferably in a major amount, most preferably in an amount of about 85 to about 95 wt. %, with the latter constituent comprising about 5 to about 15 wt. % of the mixture.

The amount of suspending agent comprising the composition will vary depending on the particular medicament and amount used, the particular suspending agent used, the nature and amounts of the other ingredients comprising the composition, and the particular viscosity values that are desired. Generally speaking, it is believed that the most widely used compositions will comprise about 1 to about 5 wt. % of the suspending agent.

The NGNA compositions of the present invention includes preferably other ingredients which impart desired properties to the composition. In some embodiments, dispersing or wetting agents are utilized. Any dispersing agent which is effective in wetting the particles and which is pharmaceutically acceptable can be used. Examples of dispersing agents that can be used are fatty alcohols, esters, and ethers, including, for example, those sold under the trademarks Pluronic, Tergitol, Span, and Tween. It is preferred to use a hydrophilic, non-ionic surfactant. Excellent results have been achieved utilizing sorbitan monooleatepolyoxyethylene which is available under the trademark Polysorbate 80.

In some embodiments, the compositions comprise an anti-oxidant. Examples of pharmaceutically acceptable anti-oxidants that can be used in the composition include ascorbic acid, sodium ascorbate, sodium bisulfite, sodium thiosulfate, 8-hydroxy quinoline, and N-acetyl cysterine. It is recommended that the composition comprise about 0.001 to about 0.01 wt. % of the anti-oxidant.

Also, for stability purposes, the NGNA compositions should be protected from microbial contamination and growth. Examples of pharmaceutically acceptable anti-microbial agents that can be used in the composition include quaternary ammonium compounds, for example, benzalkonium chloride, benzethonium chloride, cetrimide, and cetylpyridinium chloride; mercurial agents, for example, phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other antimicrobial agents such as chlorhexidine, chlorocresol, and polymyxin. It is recommended that the composition comprise about 0.001 to about 1 wt. % of the anti-microbial agent.

As mentioned above, an aspect of the present invention comprises a composition which is odorless and which contains a mixture of stabilizing agents which function as an anti-oxidant and as an anti-microbial agent. The mixture comprises a quaternary ammonium compound that has antimicrobial properties and a material which is generally recognized as a chelating agent. The use in the composition of this combination of materials with the medicament, for example, triamcinolone acetonide, results in a highly stable composition that is resistant to oxidative degradation and to the growth of bacteria and the like. In preferred form, the mixture comprises benzalkonium chloride and disodium ethylenediamine tetraacetate.

The odorless composition generally will comprise about 0.004 to about 0.02 wt. % of the quaternary ammonium compound and about 0.01 to about 0.5 wt. % of the chelating agent. By virtue of the use of the aforementioned mixture of compounds, it is not necessary to include in the composition a material which is considered an anti-oxidant.

The composition of the present invention includes preferably an iso-osmotic agent which functions to prevent irritation of nasal mucosa by the composition. Dextrose in anhydrous form is a preferred iso-osmotic agent. Examples of other pharmaceutically acceptable iso-osmotic agents which can be used include sodium chloride, dextrose and calcium chloride. It is recommended that the composition comprise up to about 5 wt. % of the iso-osmotic agent.

The pH of the NGNA compositions will vary depending on the particular medicament used and taking into account biological acceptance and the stability of the medicament. Typically, the pH of the composition will fall within the range of about 4.5 to about 7.5. The preferred pH for a composition which contains triamcinolone acetonide is about 4.5 to about 6, most preferably about 5. Examples of pharmaceutically acceptable materials which can be used to adjust the pH of the composition include hydrochloric acid and sodium hydroxide.

The NGNA compositions of the present invention can be prepared in any suitable way. In preferred form, an aqueous suspension of the solid particles of medicament and dispersing agent is formed and combined with an aqueous suspension which contains the suspending agent. The former is preferably prepared by adding the medicament to an aqueous solution of the dispersing agent and mixing thoroughly. The latter is prepared by acidifying the water (pH about 4.7 to about 5.3) prior to adding the suspending agent. In particularly preferred form, an aqueous solution of the quaternary compound (anti-microbial agent) is added to the aqueous suspension of medicament, and the other ingredients (for example, iso-osmotic agent, anti-oxidant or chelating agent) are added to the thixotropic suspension. Each of the aforementioned batches of composition is mixed thoroughly before being combined. The preferred means of combining the batches of composition is to introduce one of the batches, preferably the "medicament" batch into the bottom of the other batch, for example, by pumping the batch upwardly through the other batch. The composition comprising the combined batches is mixed thoroughly. Use of the preferred method of preparation provides an efficient and effective way for formulating a composition that has the solid particles of medicament substantially uniformly dispersed therein while avoiding problems that are generally associated with the preparation of water-based pharmaceutical compositions, for example, excessive foaming and non-uniformity of the particle dispersement.

The amount of NGNA applied to each of the nasal passages will vary depending on the nature of the condition being treated and the nature of the individual being treated. For guideline purposes, it is suggested that that unit dosage applied to one of the nasal cavities comprise about 5 micrograms to about 100 milligrams NGNA, preferably from about 100 micrograms too about 1 milligram NGNA. Use of the preferred form of the composition of the present invention provides the advantage that the composition can be applied effectively once daily.

Accordingly, the present invention provides an article of manufacture comprising a spray bottle having an NGNA solution or powder therein for delivery into a body cavity such as the nose. The spray bottle may preferably comprise a pump system for expelling the NGNA composition from the bottle, such as a compression mump, spray pump or precompression pump.

In some embodiments, the present invention provides an article of manufacture that is a device that can be worn over a body cavity such as the mouth or nose of an individual. In some embodiments, the device is mask, such as a surgical mask. In preferred embodiments, the mask comprises a solid support or matrix, such as a polymer matrix or a woven fabric matrix, into which an NGNA composition is incorporated. In some embodiments, the NGNA composition is spray coated onto the matrix as an aqueous solution, gel or powder. In some embodiments, when a breath is taken through the mask, viruses are inactivated as they contact the mask. In some embodiments, the matrix is coated with an NGNA composition to provide from about 0.01 microgram to about 100 milligram NGNA per $cm^2$ of the matrix, preferably from about 1 microgram to about 1 milligram NGNA per $cm^2$.

In some embodiments, NGNA is formulated for oral delivery. The ingredients of the supplements of this invention are preferably contained in acceptable excipients and/or carriers for oral consumption. The actual form of the carrier, and thus, the supplement itself, is not critical. The carrier may be a liquid, gel, gelcap, capsule, powder, solid tablet (coated or non-coated), tea, or the like. The supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

In some embodiments, the oral delivery vehicles described above are formulated so as to provide a daily dose of between 0.1 g and 10.0 g of NGNA, preferably between 0.5 and 2.0 g of NGNA, and even more preferably approximately 1.0 g of NGNA. In some embodiments, an effective amount of NGNA is the amount needed to inhibit the growth and proliferation of a virus of interest or to inactivate the virus. In some embodiments, the effective amount is the amount of NGNA sufficient to provide a concentration of NGNA of from about 1 nanomolar to 10 micromolar at a site of interest, such as the circulating bloodstream or in a body cavity such as the nasal passages or sinuses.

In some embodiments, NGNA is provided in a fluid that can be used for atmospheric treatment, such as by a mist. In some embodiments, the present invention provides a device comprising a reservoir, a pump, and a nozzle, wherein the reservoir comprises a fluid comprising NGNA that can be expelled via the pump through the nozzle to provide a mist comprising NGNA. In some embodiments, the device is a humidifier, while in other embodiments, the device is an automated mist dispenser. In some embodiments, the NGNA is provided as an aerosol spray in an appropriate aerosol spray dispensing device. Accordingly, in some embodiments, the present invention provides a device or composition comprising a NGNA and an aerosol propellant. Propellants include, but are not limited to, mixtures of volatile hydrocarbons, typically propane, n-butane and isobutene, dimethyl ether (DME), methyl ethyl ether, nitrous oxide, carbon dioxide and hydrofluoroalkanes (HFA): either HFA 134a (1,1,1,2,-tetrafluoroethane) or HFA 227 (1,1,1,2,3,3,3-heptafluoropropane) or combinations of the two. Typically, the NGNA fluid will be miscible with the propellant. The NGNA fluid may preferably be formulated to be an aerosol mist, foaming gel, cream or lotion.

Modern aerosol spray products have three major parts; the can, the valve and the actuator or button. The can is most commonly lacquered tinplate (steel with a layer of tin) and may be made of 2 or 3 pieces of metal crimped together. Aluminum cans are also common and are generally used for more expensive products. The valve is crimped to the rig of the can, the design of this component is important in determining the spray rate. The actuator is depressed by the user to open the valve; the shape and size of the nozzle in the actuator controls the spread of the aerosol spray.

In some embodiments, the devices of the present invention comprise a piston barrier system. Packaging that uses a piston barrier system is often used for highly viscous products such as post-foaming gels, thick creams and lotions. The main benefit of the piston barrier system is that is assures separation of the product from the propellant, maintaining the purity and integrity of the formulation throughout its consumer lifespan. The piston barrier system also provides a controlled and uniform product discharge rate with minimal product retention and is economical.

In some embodiments, the devices of the present invention comprise a bag-in-can system (or BOV "bag on valve"). This system separates the product from the pressurizing agent with a hermetically-sealed, multi-layered laminated pouch, which maintains complete formulation integrity so only pure product is dispensed. In this embodiment, the NGNA fluid is provided in the bag. Among its many benefits, the bag-in-can system extends a product's shelf life. Other advantages include all-attitude (360-degree) dispensing, quiet and non-chilling discharge.

These devices find use in setting where an antiviral spray, foam, gel or other fluid is needed. For example, the devices find use in dispensing an antiviral mist to treat a desired environment or space, such as a room in a building such as an office, kitchen, cubicle or lavatory, or a vehicle such a train car, airplane, bus, or taxi, van or car, or animal confinement facilities such as barns, abattoirs, poultry houses, etc. The devices can also be used to dispense NGNA containing fluids on a surface such as a countertop, floor, shower, etc. In some embodiments, the devices are used to inject the NGNA-containing mist into the ventilation system of a building, barn, or vehicle.

In still further embodiments, the present invention provides NGNA compositions that comprise NGNA in a solution, such as a normal saline solution, that can be applied to the eye. Accordingly, in some embodiments, the present invention provides an article of manufacture comprising a container equipped with a nozzle to provide drops of an NGNA solution to the eye. It is contemplated that in addition to effects in the eye and surrounding tissue, NGNA administration via the eye and tear channel will directly access the sinuses and associated cavities. Thus, administration of NGNA and/or additional antimicrobials or antivirals in eyedrops is an effective method of administration of NGNA or other compounds for the treatment of eye infections, sinus infections, and systemic treatment via the eye and tear channel, and sinuses, mucus internal surfaces for effective adsorption providing local and systemic treatments.

In other embodiments, the NGNA is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

In some embodiments, the NGNA is provided in water that is supplied to farm animals, such as poultry, cattle, swine, sheep and the like, or used in water used in fisheries. In other embodiments, NGNA is provided in tap water or water bottles water for human use.

The NGNA compositions may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the compositions of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the compositions further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

D. Dietary Supplements

The present invention provides dietary supplements comprising nutraceutical agents, preferably NGNA either by itself or in combination with one or more additional nutraceuticals agents. Nutraceutical agents are natural, bioactive chemical compounds that have health promoting, disease preventing or medicinal properties. Examples of nutraceuticals include, but are not limited to, *Allium Cepa, Allium Sativum, Aloe Vera, Angelica* Species, *Naturally Occurring Antioxidants, Aspergillus Oryzae Enzyme Therapy, barley grass, Bromelain, Carnitine, Carotenoids* and *Flavonoids, Catechin, Centella Asiatica* (Gotu kola), Coenzyme Q10, Chinese Prepared Medicines, *Coleus Forskohlii, Commiphora Mukul, Conjugated Linoleic* Acids (CLAs), *Crataegus Oxyacantha* (Hawthorne), *Curcuma Longa* (Turmeric), *Echinacea* Species (Purple Coneflower), *Eleutherococcus Senticosus* (Siberian Ginseng), *Ephedra* Species, Dietary Fish Oil Consumption and Fish Oil Supplementation, *Genistein, Ginkgo Biloba, Glycyrrhiza* (Licorice), *Hypericum Perforatum* (St. John's Wort), *Hydrastis* (Goldenseal) and Other Berberine-Containing Plants, *Lactobacillus, Lobelia* (Indian Tobacco), *Melaleuca Alternifolia, Menaquinone, Mentha Piperita*, n-glycolylneuraminic acid (NGNA), *Panax Ginseng, Pancreatic Enzymes, Piper Mythisticum, Procyanidolic Oligomers, Pygeum Africanum, Quercetin, Sarsaparilla* Species, *Serenoa Repens* (Saw palmetto, Sabal serrulata), *Silybum Marianum* (Milk Thistle), Rosemary/Lemon balm, *Selenite, Tabebuia Avellanedae* (LaPacho), *Taraxacum*

*Officinale, Tanacetum Parthenium* (Feverfew), *Taxol, Uva Ursi* (Bearberry), *Vaccinium Myrtillus* (Blueberry), *Valerian Officinalis, Viscum Album* (Mistletoe), Vitamin A, Beta-Carotene and Other *Carotenoids*, and *Zingiber Officinale* (Ginger).

Several nutraceutical agents are used in treating viral disorders (e.g., Genistein (in soy/red clover), rosemary/lemon balm, selenite, barley grass, lauric acid, *Phyllanthus amarus/niruri* (see, e.g., Nicolson, G. (1998) J. Medicine 1:123-128; herein incorporated by reference in its entirety). Additional anti viral nutraceutical agents include, but are not limited to, catechins, flavenoids, Echinacea, cascara, and NGNA.

In preferred embodiments, the present invention provides compositions comprising dietary supplements (e.g., NGNA) for inducing physiological responses such as alleviating the symptoms of viral-induced obesity, alleviating or treating the symptoms of colds, preventing the onset of colds, increasing energy and increasing the feeling of well-being in subjects. Such compositions may contain, for example, between 0.1 g and 10.0 g of dietary supplements (e.g., NGNA), preferably between 0.5 g and 2.0 g of dietary supplements (e.g., NGNA), and even more preferably, approximately 1.0 g of dietary supplements (e.g., NGNA). Furthermore, dietary supplements (e.g., NGNA) are preferably provided in an amount sufficient to induce the physiological response desired (e.g., alleviation of the symptoms of viral-induced obesity, alleviation of the symptoms of colds, prevention of the onset of colds, increasing energy and increasing the feeling of well-being in subjects). In some embodiments, the compositions are provided for use in inducing one of the foregoing responses, while in other embodiments, the compositions are provided for use in inducing two or more of the foregoing responses.

The present invention further provides methods for treating the physiological conditions discussed above (e.g., conditions such as obesity, periodic weight gain, lack of energy, mild depression, colds, etc.). In preferred embodiments, dietary supplements are used in treating viral induced obesity. In other preferred embodiments, dietary supplements are used in treating infection caused by a virus that causes viral obesity (e.g., Ad-36). In other preferred embodiments, dietary supplements are used in preventing viral related obesity through targeting of viruses that cause viral obesity (e.g., Ad-36, Ad-36p, SMAM-1). In some embodiments, the compositions are provided for use in treating one of the foregoing conditions, while in other embodiments, the compositions are provided for use in treating two or more of the foregoing conditions.

The dietary supplements of the present invention are further used in conjunction with a weight loss diet regimen. The present invention is not limited to a particular kind of weight loss diet regimen (e.g., exercise, reduced calorie intake, etc.). In preferred embodiments, the weight loss diet regimen is a dietary plan (e.g., Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, and Zone diet. In still other preferred embodiments, the weight loss diet regimen is an exercise plan (e.g., running, swimming, meditation, yoga, hypnosis, clinical therapy, bicycling, walking, etc.). In still other preferred embodiments, the weight loss diet regimen is a clinically assisted plan (e.g., hypnosis, rehabilitory training, a dietary plan provided through a dietician, surgical procedures, etc.).

The dietary supplements of the present invention may further be administered in any form (e.g., pill, food product, etc.). In preferred embodiments, the dietary supplements are provided as a beverage, bar, powder, pill, or shake (e.g., a nutritional supplement as described in more detail below).

The dietary supplements of the present invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., approximately 1 g of a nutraceutical agent) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals. In preferred embodiments, a dietary supplement increases satiety and results in a decrease in caloric intake and subsequent weight loss. In particularly preferred embodiments, a dietary supplement regulates viruses (e.g., adenoviruses).

E. Nutritional Supplements

In other embodiments, the present invention provides nutritional supplements (e.g., energy bars or meal replacement bars or beverages) comprising NGNA. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids).

Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the nutritional supplement preferably contain between 0.1 g and 10.0 g of NGNA, preferably between 0.5 and 2.0 g NGNA, and even more preferably approximately 1.0 g NGNA. It is understood by those of skill in the art that other ingredients can be added to those described herein, for example, fillers, emulsifiers, preservatives, etc. for the processing or manufacture of a nutritional supplement.

F. Food Products

In still further embodiments, the present invention provides functional foods, including food products, prepared food products, or foodstuffs comprising nutraceutical agents. For example, in some embodiments, beverages and solid or semi-solid foods comprising nutraceutical agents are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

Servings of the food product preferably contain between 0.1 g and 10.0 g of NGNA, preferably between 0.5 and 2.0 g of NGNA, and even more preferably approximately 1.0 g of NGNA.

G. Administration to Animals

In some embodiments, the present invention contemplates administration of NGNA to animals. Preferred animals include, but are not limited, poultry, fish, companion animals such as dogs and cats, horses, swine, and ruminants such as cattle and sheep. The NGNA may be administered for any of the purposes described above, e.g., prevention of viral infection, treatment of viral infections, etc. In some preferred embodiments, the present invention provides NGNA compositions methods of using NGNA compositions for use in animals for the prevention and/or treatment of viral infections caused by members of the following families of viruses: Picornaviridae, Caliciviridae, Adenoviridae, Herpesviridae, and Orthomyxoviridae. Exemplary formulations are described in detail above. However, in some embodiments, NGNA is formulated as a lotion, spray, gel, ointment, powder, aqueous or non-aqueous solution for topical, intranasal, intravaginal, intraanal, or sublingual administration; as a capsule, powder, or tablet for enteral administration; or as a solution for parenteral administration. In some embodiments, the NGNA is preferably provided as a component of a powder that can be dissolved in a water supply for animals, or used to bathe animals. In some embodiments, the NGNA is provided as a liquid that can be aerosolized or misted into a barn or other enclosure containing animals. In other embodiments, the NGNA is supplied as a solution that can be injected into a water system designed for animals.

In some embodiments, the present invention provides animal feeds comprising NGNA. The animal feeds are preferably formulated as in known in the art. Exemplary animal feeds include diets formulated for poultry, fish, companion animals such as dogs and cats, horses, swine, and ruminants such as cattle and sheep. In some embodiments, the NGNA is provided as a supplement that can be incorporated into animal feeds as they are being mixed or manufactured. In preferred embodiments, the feeds are formulated so as to provide a daily dose of between 0.1 g and 10.0 g of NGNA, preferably between 0.5 and 2.0 g of NGNA, and even more preferably approximately 1.0 g of NGNA.

EXAMPLES

Example 1

A sports drink containing NGNA was formulated for use by humans. The NGNA was made from glucosamine residues derived from crab chitin. The finished drink (per 500 ml bottle) contained: pure water; 1% Glycerol/(0,1-10%); lemon flavor; potassium sorbate/sodium benzoate as stabilizers; and 2 mg of 99% pure NGNA.

Example 2

Figure 1B:
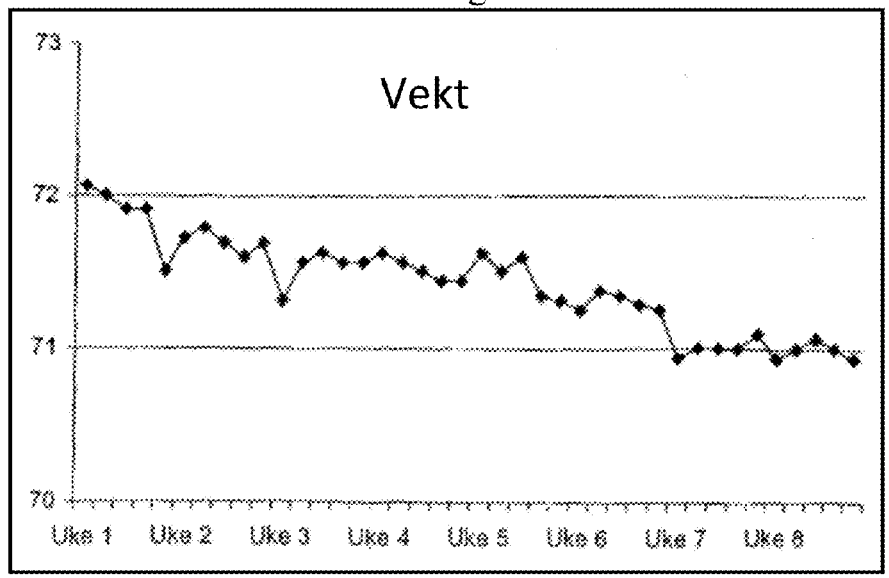
FIG. 1b is a graph showing a decrease in average weight of the subjects involved in the study.
Figure 2A:
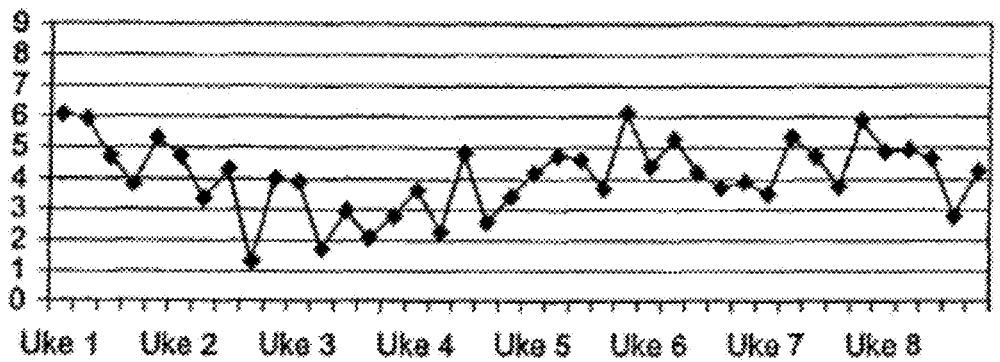
FIGS. 2a-f provide graph of responses over the eight week (Uke) period of the NGNA sport drink study to the following questions.
Figure 2B:
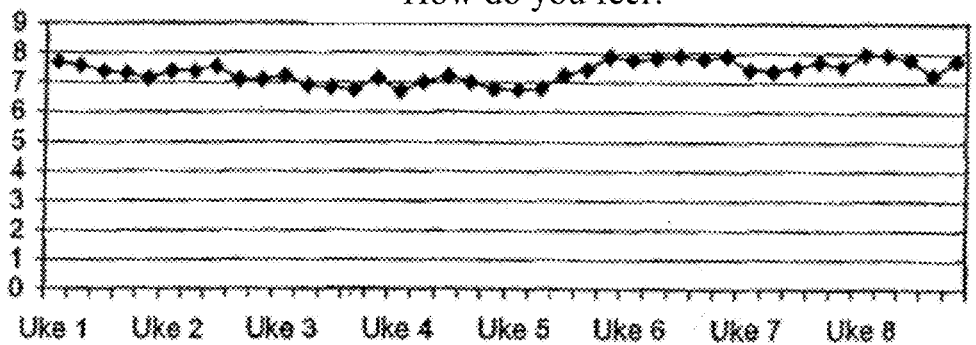
Figure 2C:
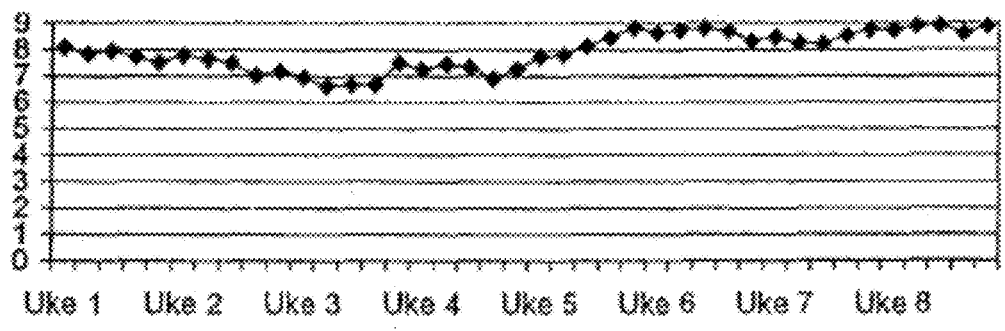
Figure 2D:
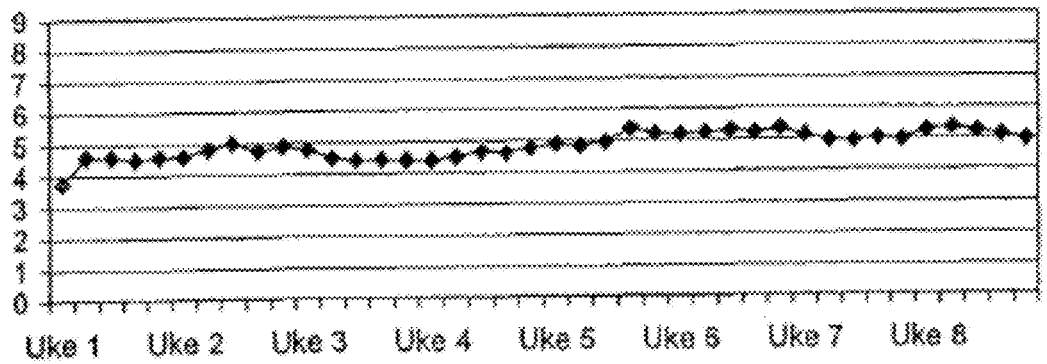
Figure 2E:
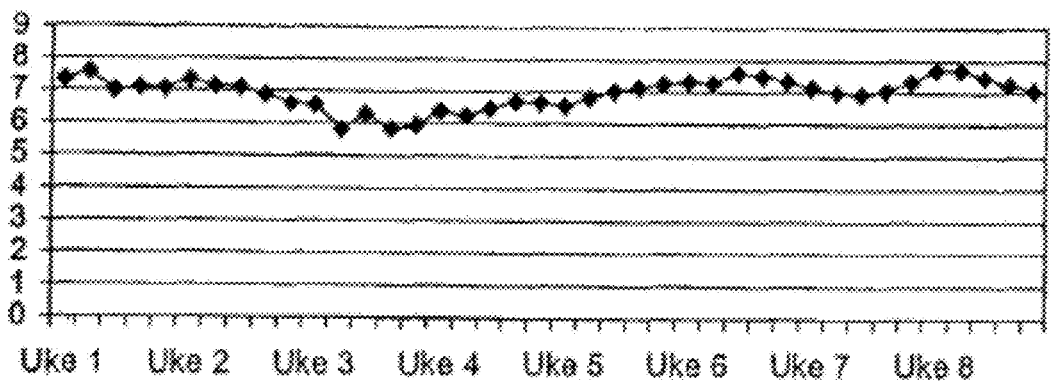
Figure 2F:
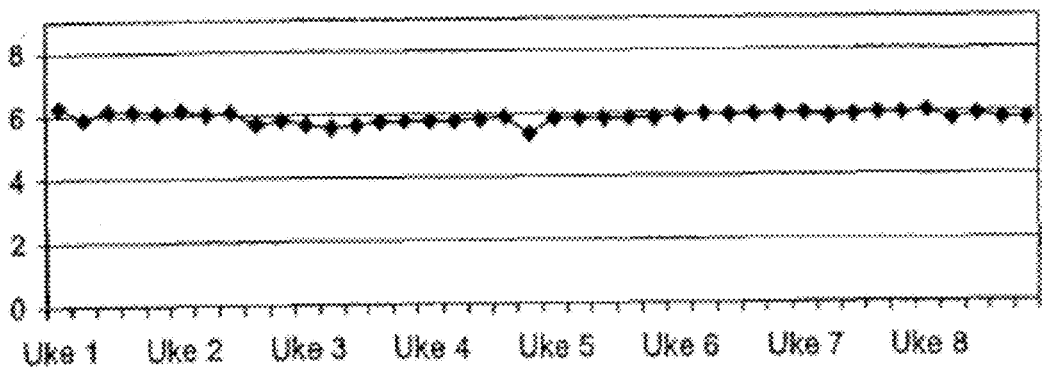

The sports drink described in Example 1 was tested in a group of 18 subjects. The subjects were supplied one 500 ml bottle of the sport drink containing 2 mg NGNA. The drink was administered during exercise or during the day when not exercising over an eight week period. The subjects worked out an average of about four times per week. The following measurements were taken during the study: fett/fat %, vekt/weight, overarm/upper arm in cm, midje/waist in cm, lar/thighs in cm. These results are summarized in FIG. 1A. As can be seen, there was a steady decrease in weight during the study (FIG. 1B). The subjects were also asked to evaluate other physiological effects of the drink. The subjects were asked to rank the impact of the drink on a scale of 0 to 9 (with 9 being a positive impact) with respect to the following questions:
  a. How was your workout today
  b. How do you feel?
  c. Do you have a cold 0, or are you healthy 9?
  d. Do you feel the drink helps you?
  e. How is workout energy and joy?
  f. Do you like the sport drink?
The results are presented in FIGS. 2a-f, respectively. As can be seen, there were positive responses for well-being, colds, and energy/workout joy.

Example 3

This example describes the in vitro inhibition of various viruses by compositions comprising NGNA.
Influenza
  The Influenza B virus that will be used for this study will be B/Malaysia.
  Source: Retroscreen Virology Ltd. Virus B/Malaysia/2506/2004
  Physical form: Virus in liquid medium
  Expiry date: 4 hours after dilution
  Storage conditions: On ice
  Safety precautions: Biosafety Level 2 containment conditions
  The cell line to be used in Phase A is MDCK cells. The Growth Media for the MDCK cell line is DMEM, 2 mM L-Glutamine, 10% FBS (foetal bovine serum) and 2 mM Hepes buffer. The Infection Media for the MDCK cell line is DMEM, 2 mM L-Glutamine, 2 mM Hepes buffer and 1.5 mM Trypsin (TPCK treated).
  In the virucidal assay the Influenza B virus titrations will be incubated for 2 to 3 days before the efficacy of the test article on the virus will be determined by HA (Haemagglutination Assay). This assay utilizes the ability of influenza virus to bind red blood cells to determine the presence or absence of virus in a given well on the titration plate.
  The method for this procedure is as follows:
    After the 3 days incubation period of the virus titrations from the virucidal assay (see section 8.1.1.3), 50 μL of the supernatant from each well on the 96-well titration plate will be transferred to the corresponding well on a fresh v-bottomed 96-well assay plate.
    50 μL of 0.5% turkey red blood cells in PBS (v/v) will then be added to each well on the v-bottomed assay plate to give a total volume of 100 μL.
    The virus/red blood cell suspensions will be mixed by placing the plates on a plate shaker for approximately 30 seconds at 200-400 rpm.
    The plates will then be incubated at room temperature for approximately 30 minutes before being read visually for the presence of virus in each well.
    Each well will be scored positive or negative. Briefly, haemagglutination of the red blood cells will indicate a positive result and sedimentation of the red blood cells into the apex of v-shaped well will indicate a negative result.
Herpes Simplex Type 1 (HSV-1)
  The Herpes Simplex virus that will be used for this study is HSV-1.
  Source: Retroscreen Virology Ltd. Virus HSV-1, SC-16
  Physical form: Virus in liquid medium
  Expiry date: 4 hours from dilution
  Storage conditions: On ice
  Safety precautions: Biosafety Level 2 containment conditions
  The cell line to be used in Phase B is Vero cells. The Growth Media for the Vero cell line is DMEM, 2 mM L-Glutamine, 10% FBS (foetal bovine serum) and 2 mM Hepes buffer. The Infection Media is the same as the Growth Media. In the virucidal assay HSV-1 titrations will be incubated for 3 days before the efficacy of the test article on the virus can be determined by CPE.
Rhinovirus
  The Rhinovirus that will be used for this study is HRV-16
  Source: Retroscreen Virology Ltd.Virus HRV-16
  Physical form: Virus in liquid medium
  Expiry date: 4 hours after dilution
  Storage conditions: On ice
  Safety precautions: Biosafety Level 2 containment conditions
  The cell line to be used in Phase C is Wi-38 cells. The Growth Media for the Wi-38 cell line is DMEM, 2 mM L-Glutamine, 10% FBS (foetal bovine serum). The Infection Media for the Wi-38 cell line is DMEM, 2 mM L-Glutamine, 2% FBS (foetal bovine serum) and 10 mM $MgCl_2$.
  In the virucidal assay, *Rhinovirus* titrations will be incubated for 4-7 days before the efficacy of the test article on the virus can be determined by CPE.
Adenovirus
  The Adenovirus that will be used for this study is AD-5
  Source: Retroscreen Virology Ltd. Virus AD-5
  Physical form: Virus in liquid medium
  Expiry date: 4 hours from dilution
  Storage conditions: On ice
  Safety precautions: Biosafety Level 2 containment conditions
  The cell line to be used in Phase D is MRC-5 cells. The Growth Media for the MRC-5 cell line is EMEM, 2 mM L-Glutamine, 10% FBS (foetal bovine serum) and 1× NEAA (non-essential amino acids). The Infection Media for the MRC-5 cell line is EMEM, 2 mM L-Glutamine, 2% FBS (foetal bovine serum) and 10 mM $MgCl_2$. In the virucidal assay Adenovirus titrations will be incubated for 7-10 days before the efficacy of the test article on the virus can be determined by CPE.
Norovirus Surrogate Virus
  The Norovirus-surrogate virus that will be used for this study is Feline Calicivirus (FCV).
  Source: Retroscreen Virology Ltd. Virus Feline Calicivirus (FCV) (substitute for norovirus)
  Physical form: Virus in liquid medium
  Expiry date: 4 hours from diluting Storage conditions: On ice
Safety precautions: Biosafety Level 2 containment conditions The cell line to be used in Phase E is CRFK (Crandell-Reese feline kidney) cells. The Growth Media for the CRFK cell line is EMEM, 2 mM L-Glutamine, 10% FBS (foetal bovine serum). The Infection Media for the CRFK cell line is EMEM, 2 mM L-Glutamine, 2% FBS foetal bovine serum). In the virucidal assay FCV titrations will be incubated for 3 to 5 days before the efficacy of the test article on the virus can be determined by CPE.

Methods

N-Glycolylneuraminic acid (test article) will be tested for the ability to inhibit the viruses identified above. The physical form of NGNA is a HPLC purified dry powder, Molecular weight 325.268. In the virucidal assay 9 volumes of test article is added to one volume of virus. Therefore, when the virus is mixed with the test article the resulting final concentration of the test article will be at 90% (v/v). The test article comes in the form of an off white powder, this will be initially dissolved in dH2O to generate a stock solution before working concentrations are made by subsequent dilution in Infection media.

Controls. The controls to be utilized in the virucidal assay are:

Cell only control—Cells not infected with virus. This will be a negative control for vCPE (viral cytopathic effect) and is also an indicator of cell quality.

Virus only control—Cells infected with cell infection media that has been treated with virus in the same way as the test articles. This will be a positive control for vCPE.

Antiviral control—Cells infected with virus pre-treated with citrate buffer solution, 0.09 M, pH 3.5. This will be a positive control for the test articles.

Cytotoxicity testing. The test article will be assessed as follows:

A 100 µM solution of the compound SCN-KI-NSG will be made using the Infection media relevant to each cell line used in this study for the viruses being tested (see details for separate phases in section 8.1). Each cell line in use will be tested.

Cells will be seeded into a 96-well plate the day prior to use in the assay.

All the media will be removed from the first row, and 111 µL of either the test (100 µM SCN-KI-NSG) or control articles will be added in quadruplicate to the wells.

The test/control articles will be titrated in a 10-fold dilution series for a further 10 rows.

The last row of wells will be used as the cell only control.

The cells will be then incubated for 4 hours at 37oC with 5% CO2.

After the incubation period, each well will be checked for tCPE.

The tCPE data will be used to determine the highest concentration of test article that can be used in the virucidal assay before cytotoxic effects of the test article on the cells would interfere with the interpretation of the virucidal assay data.

The results of the cytotoxicity assay will be discussed with the sponsor prior to commencing the virucidal assay, such that an agreement is reached on what concentrations to use in the virucidal assay.

Virucidal testing. The virucidal assay will be performed as described below. A single time point of 10 minutes will be used for each of the 3 different concentrations of test article to be tested.

Testing Protocol.

Add 360 Ml of test article at the required test concentration to 40 Ml of virus (Total volume=400 ML)

Vortex to mix and incubate at room temperature for 10 minutes

Terminate the reaction by dilution with the addition of 3.6 mL infection media (Total volume=4 mL)

Inoculate the terminated reaction onto the cell monolayer in quadruplicate and titrate residual virus by 10-fold serial dilution Incubate the cells for 2-7 days (as required for the specific phase, see section 8.1) at 37° C., 5% $CO_2$.

Confirm the residual virus titer using vCPE and/or Haemagglutination Assay.

Results.

| Virus | Cell Line | Sample | Sample titer ($\log_{10}$ $TCID_{50}$/ml) | Control virus titer ($\log_{10}$ $TCID_{50}$/ml) | Virus reduction (%) |
|---|---|---|---|---|---|
| Influenza B | MDCK | NGNA 10 mM | 2.50 | 4.50 | 99.00 |
| Influenza B | MDCK | NGNA 10 µM | 4.50 | 4.50 | 0.00 |
| Influenza B | MDCK | NGNA 10 nM | 4.50 | 4.50 | 0.00 |
| Influenza B | MDCK | Citrate buffer (+control) | 2.50 | 4.50 | 99.00 |
| HSV-1 | Vero | NGNA 10 mM | 2.50 | 6.25 | 99.98 |
| HSV-1 | Vero | NGNA 10 µM | 6.25 | 6.25 | 0.00 |
| HSV-1 | Vero | NGNA 10 nM | 7.00 | 6.25 | 0.00 |
| HSV-1 | Vero | Citrate buffer (+control) | 2.50 | 6.25 | 99.98 |
| HRV | Wi-38 | NGNA 10 mM | 2.50 | 4.75 | 99.44 |
| HRV | Wi-38 | NGNA 10 µM | 3.50 | 4.50 | 90.00 |
| HRV | Wi-38 | NGNA 10 nM | 3.50 | 4.50 | 90.00 |
| HRV | Wi-38 | Citrate buffer (+control) | 2.50 | 4.75 | 99.44 |
| FCV | CRFK | NGNA 10 mM | 4.50 | 5.25 | 82.21 |
| FCV | CRFK | NGNA 10 µM | 5.50 | 5.50 | 0.00 |
| FCV | CRFK | NGNA 10 nM | 5.50 | 5.50 | 0.00 |
| FCV | CRFK | Citrate buffer (+control) | 4.50 | 5.25 | 82.11 |

Example 4

The overall purpose of the study was to determine whether the N5G nutritional supplement has the ability to have significant impact on clinical disease outcomes caused by influenza virus in a mouse animal model.

The experimental design included adherence to a strict feeding schedule, which included 30 days of acclimation of mice to a defined base feed (AIN-93M) provided by Purina TestDiet, Inc. Control animals remained continuously fed with the defined base feed, while the experimental mouse group was fed with the base feed supplemented with 0.35% of NSG.

Experimental and control mouse groups were infected intranasally with 107.5 TCID50 influenza A (H1N1) with each mouse receiving 5 iL of viral inoculum per nostril. The experimental parameters followed during the study were: 1) mouse weight changes; 2) food intake changes; 3) clinical signs of disease; 4) lung tissue pathology; 5) lung consolidation scores; 6) changes in viral loads.

Overall, the experimental design was executed without any major obstacles. As expected, there was minor occasional wasting of feed in some cages (mice chewed on feed which was dropped on the bottom of the cage). In every instance noted on daily observations, the residual feed was weighed, but it was excluded in any statistical calculations as well as in the calculation of baseline feed intake.

SUMMARY OF FINDINGS

As expected, all influenza infected mice developed clinical signs of disease starting 2 days post infection. Clinical signs included: 1) ruffled fur, 2) inactivity, 3) hunching, 4) death, 5) weight loss, and 6) loss of appetite.

Clinical signs 1-4 were scored by two independent observers using a scale of 0-5. The cumulative scores were plotted and statistically analyzed. Statistical analyses were performed using SAS v.9.1.3. An analysis of variance (ANOVA) of a repeated measures design was calculated in a split-plot arrangement of treatments, with the treatment group on the main plot, and the subplot including day and treatment by day interactions. Interaction of pairwise comparisons of least square means was performed with a pairwise t-test with pre-planned comparisons. This statistical methodology was used for all comparisons in the study.

A. Statistically significant differences were reported in the treated versus untreated scores in the time interval spanning days 6-8 and post infection for clinical signs 1-4 (FIG. 3). Specifically, it was noted that mice individual mice fed with N5G appeared substantially healthier than control mice as evidenced primarily by ruffled fur, lethargy and hunching posture changes.

B. Measurements of feed intake revealed a statistically significant loss of appetite as revealed by the drop in % daily feed intake especially noted in the time span of days 5-6 post infection (FIG. 4).

C. The most dramatic change in treated versus untreated mice was the noted %change in mouse weights of untreated versus treated (N5G fed) mice. A highly significant reduction in body weights was observed in the control mouse group in the time span between days 3-9 post infection (FIG. 5).

D. The most important aspect of influenza infections is the resultant lung immunopathology. Typically, viral replication as well as infiltration of lymphocytes causes substantial damage to lung tissues. In fact, it is believed that infiltration of lymphocytes and their negative effects on lungs tissues is the most important parameter of influenza-related morbidity and mortality in humans. Consequently, particular care was taken to examine the tissues of mice for signs of histopathological changes. The following evaluation criteria were utilized to score these changes: 1) Lung consolidation scores (LCS); 2) Histopathological scores (HS). LCS were rated as follows: grade 1: no plum coloration; grade 2: minimum plum coloration; grade 3: medium plum coloration; grade 4: maximum plum coloration. HS were rated as follows: Grade 0: no overt histological change; grade 1+: only bronchial/bronchiolar and/or peri-bronchial/bronchiolar/vascular changes; grade 2+: 1-10% pulmonary parenchyma affected; grade 3+: 11-30% pulmonary parenchyma affected; grade 4:+: 31-50% pulmonary parenchyma affected; grade 5+: greater than 50% pulmonary parenchyma affected.

a. Lung consolidation scores revealed a "trend" toward a healthier status of treated versus untreated mice. However, there results were not statistically significant (FIG. 6).

b. Histopathological scores revealed a statistically significant difference in treated versus untreated mice at day 6 post infection (FIG. 7).

E. Viral titers were obtained from lung homogenates starting at day 2 post infection (days 2, 4, 6, 8 and 21). No significant differences were observed in treated versus untreated mice, while viral titers obtained at 2 days post infection were less than 100 plaque forming units (PFU) per 250 iL of homogenate (the lungs were homogenized to produce a 1 mL-total homogenate). No statistical analysis could be applied to viral titers since only one mouse per group per time point was tested.

Overall Conclusion

The obtained results collectively indicate a significant effect of N5G on ameliorating clinical symptoms and adverse pathological implication of influenza infection in the mouse experimental model.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for treating rhinovirus infection in a human or animal subject comprising providing a composition comprising n-glycolylneuraminic acid in an concentration of 1 nM to 10 mM, and intransally administering said composition under conditions such that rhinovirus infection is treated.

2. The method of claim 1, wherein said composition is selected from the group consisting of gels, solutions, sprays, powders, creams, foams and lotions.

* * * * *